United States Patent
Haensch et al.

(10) Patent No.: US 7,088,876 B2
(45) Date of Patent: Aug. 8, 2006

(54) FREQUENCY COMB ANALYSIS

(75) Inventors: Theodor W. Haensch, Munich (DE); Michael Mei, Munich (DE); Ronald Holzwarth, Munich (DE); Frederick R. Blume, Wenham, MA (US)

(73) Assignee: Menlo Biocombs, Inc., Boston, MA (US)

( * ) Notice: Subject to any disclaimer, the term of this patent is extended or adjusted under 35 U.S.C. 154(b) by 0 days.

(21) Appl. No.: 11/343,342

(22) Filed: Jan. 30, 2006

(65) Prior Publication Data

US 2006/0132784 A1 Jun. 22, 2006

Related U.S. Application Data (62) Division of application No. 11/096,311, filed on Mar. 31, 2005, which is a division of application No. 10/121,983, filed on Apr. 12, 2002, now Pat. No. 6,897,959.

(60) Provisional application No. 60/283,773, filed on Apr. 13, 2001.

(51) Int. Cl.
 *G02F 1/295* (2006.01)
(52) U.S. Cl. ............................................ 385/4; 372/23
(58) Field of Classification Search ............... 385/4; 359/238, 615; 372/23, 26
 See application file for complete search history.

(56) References Cited

U.S. PATENT DOCUMENTS

| 4,035,643 A | 7/1977 | Barrett |
| 4,297,035 A | 10/1981 | Bjorklund |
| 4,491,747 A | 1/1985 | Shimizu |
| 4,937,457 A | 6/1990 | Mitchell |
| 5,166,822 A | 11/1992 | Priatko et al. |
| 5,784,157 A | 7/1998 | Gorfinkel et al. |
| 5,907,417 A | 5/1999 | Darcie et al. |
| 6,014,237 A * | 1/2000 | Abeles et al. .................. 398/87 |
| 6,201,638 B1 | 3/2001 | Hall et al. |
| 6,731,838 B1 | 5/2004 | Dueck et al. |
| 6,785,303 B1 * | 8/2004 | Holzwarth et al. .......... 372/100 |
| 2002/0068018 A1 | 6/2002 | Pepper et al. |
| 2002/0196509 A1 * | 12/2002 | Smilanski et al. .......... 359/188 |
| 2003/0039437 A1 | 2/2003 | Boord et al. |

* cited by examiner

*Primary Examiner*—Gregory J. Toatley
*Assistant Examiner*—Kara E. Geisel
(74) *Attorney, Agent, or Firm*—Edwards Angell Palmer & Dodge LLP (57) ABSTRACT

Methods and apparatus for generating a frequency comb and for its use in analyzing materials and in telecommunications. The frequency comb is generated by passing pulsed light from a laser through an optical fiber having a constriction. The frequency comb comprises a plurality of monochromatic components separated in frequency by a substantially constant frequency increment. The monochromatic components are used to probe materials for analysis. In preferred embodiments, the materials are DNA, RNA, PNA and other biologically important molecules and polymers. Optical responses are observed and used to analyze or identify samples. In telecommunication applications, the individual monochromatic components serve as carriers for individual communication channels that can carry information of any of a variety of types, such as voice, data and images.

6 Claims, 6 Drawing Sheets

FREQUENCY COMB ANALYSIS

CROSS-REFERENCE TO RELATED APPLICATIONS

This application is a divisional application of U.S. patent application Ser. No. 11/096,311, filed Mar. 31, 2005, which is a divisional application of U.S. patent application Ser. No. 10/121,983, filed Apr. 12, 2002, now U.S. Pat. No. 6,897,959, which claims the benefit of U.S. provisional application Ser. No. 60/283,773, filed Apr. 13, 2001, the disclosure of which is incorporated herein by reference in its entirety.

FIELD OF THE INVENTION

The invention relates to methods and materials for analyzing and characterizing samples and for improving optical communications.

BACKGROUND OF THE INVENTION

Optical frequency pulsing has a host of diverse uses. However, there are two principal categories into which optical frequency pulsing may conveniently be placed. A first has to do with using frequency pulsing to encode information for transmission across fiber optic lines. A second broad category of use for optical frequency pulsing is the identification of physical properties of molecules. Each of these uses of optical frequency pulsing has limitations that have prevented full exploitation of the technology.

For example, a limitation in the use of optical frequency pulsing for transmission of information is the relatively wide bandwidth of individual frequency pulses, resulting in overlapping pulses over large transmission distances. As frequency pulses proceed along a fiberoptic line, pulse width increases. Over fairly modest distances, the overlap of frequency lines can result in a loss of digital information content. Another limitation is the difficulty in generating a plurality of different, closely spaced frequencies which limits signal resolution.

The identification and characterization of physical substrates using frequency pulses is limited by the ability to provide sufficiently narrow, stable pulses at high frequency in order to obtain precise physical chemical resolution of the target substrate. Typical methods for optical analysis of substrates involve interferometric measurements. Such measurements necessarily result in decreased resolution in space and time. Therefore, interferometric measurements are less than ideal.

There is a need in the art to provide optical frequency pulse methodology that provides pulses having narrow line width, wide spectral width and high repetition rate in order to enable efficient optical communications and detection high-resolution detection of physical substrates.

SUMMARY OF THE INVENTION

The present invention provides frequency combs, and materials and methods for generating frequency combs and methods of their use. The invention is useful for both optical analysis of physical substrates and optical communications. Methods of the invention comprise use of optical frequency combs to generate a series of discrete emission lines that can extend across the optical spectrum or a portion thereof. Because the frequency lines are narrow, are spaced-apart, and cover a suitable frequency bandwidth, they are useful to conduct optical communications over long distances as well as to generate precise light frequencies used in substrate identification and analysis.

According to the invention, a frequency comb is generated by firing a laser pulse into a photonic structure having a small cross-section, preferably a tapered photonic tube or fiber, resulting in a series of spaced apart, preferably regularly spaced-apart, discrete emission lines extending across at least a portion of the spectrum produced by the original laser pulse. The frequency comb represents the Fourier transform of a train of short pulses of a single wavelength of light. In a preferred embodiment, the frequency comb is generated using a train of laser pulses, each pulse having a duration of between $10^{-12}$ and $10^{-18}$ seconds, preferably between 1 picosecond and 1 femtosecond, that is passed through an optical fiber having a constriction between about 1.8 microns to about 1.5 microns, and preferably about 1.7 microns diameter.

In one embodiment, at least one monochromatic component or spectral line of the frequency comb, once generated, is focused by, for example a lens, onto a substrate for identification and/or analysis. The frequency comb may be focused to a single point for detection of a discrete molecular entity. For example, in a preferred embodiment, frequency combs are used to determine the identity of individual nucleic acids in a linearized strand of deoxyribonucleic acid (DNA). The use of frequency combs enables detection of the sequence of DNA where detection with single-source light would not be possible. Each monochromatic component of the frequency comb comprises photons having energy E that is proportional to frequency, represented by $E=h\nu$. A substance to be analyzed, such as a nucleic acid, absorbs a photon of a specific frequency corresponding to an energy transition in the nucleic acid. Observation of absorption of photons of the specific frequency provides information about the identity of the nucleic acid in question. Pulses of extremely short duration, such as pulses in the range of 1 picosecond to less than 10 femtoseconds, interact with the substance in time periods so short that the substance has insufficient time to undergo chemical reaction or even to vibrate. Accordingly, frequency combs of the invention allow a selection of frequency components best suited to identify the target sample. In fact, the number of emission lines produced by the average frequency comb, along with the ability to rapidly pulse a sample, allows redundant probing of the sample to increase the specificity of detection. A frequency spacing of approximately 10 GHz between monochromatic components of a frequency comb generated with a laser having a wavelength of approximately 800 nm has monochromatic components that differ in wavelength by dimensions of the order of 0.1 Angstroms.

A sample may be exposed to multiple illumination prior to detection. Illumination of a sample preferably comprises pulsed illumination at a frequency in the range of approximately $10^{12}$ per second to approximately $10^{18}$ per second. The pulsed illumination preferably has a pulse duration that is in the range of about one picosecond to less than about ten femtoseconds. In a more preferred embodiment, the pulse duration is less than about one femtosecond. In an alternative embodiment, the illumination is continuous.

Due to the nature of the invention, the invention may be used to detect any sample upon or through which light can be projected. Similarly, the invention can be used to elucidate any sample characteristic, including but not limited to the identity of the sample, its chemical composition, its state, its three-dimensional structure, its phase, and similar characteristics.

Methods of the invention generally comprise an illuminating step. Illuminating can encompass many forms. For example, the illuminating step may comprise illuminating the sample with a plurality of spectral lines in sequence. Alternatively, the illuminating step comprises the step of combining a plurality of spectral lines.

The sample may be prepared for analysis prior to exposure to the frequency comb. For example, samples may be prepared by treatment with a chromophore. Alternatively, the sample may be labeled with labels other than a chromophore that can interact with light, for example a substance having optical rotatory power. The sample for analysis can be selected from a variety of substances, including tissue, nucleic acid, protein, cells, metal, minerals, and other molecules and compositions. The determining step of the analysis includes comparing the response to one or more responses, each associated with a known characteristic, which can be determined empirically or by reference to known standards.

In another aspect, the invention features a method for determining the identity of a sample. The method comprises the steps of generating a frequency comb comprising a plurality of monochromatic spectral lines, illuminating a sample with at least one of the spectral lines, detecting a response to the illuminating step produced by the sample, and determining the identity of the sample based upon the response. In methods of determining the identity of a sample, the determining step comprises comparing the response to one or more responses, each known to be associated with an identified sample.

In either the method of analyzing a sample or the method of determining the identity of a sample, the step of generating a frequency comb can involve passing monochromatic light through an optical waveguide having at least one constriction therein.

A preferred method of using frequency combs of the invention is the sequencing of a polymer, such as DNA. In general, a linearized DNA is passed through a channel comprising a detection zone. Light (i.e., at least one of the multiple emission lines) produced by the frequency comb is concentrated at the detection zone where it comes into contact with a single nucleotide. Preferably, the single nucleotide is pulsed by the frequency comb at a desired frequency. At least one spectral response produced from the nucleotide is detected by a spectrometer, a spectrophotometer, a CCD detector, or similar device for the detection of light spectra. The detected spectral response is characteristic of the nucleotide that was probed by the frequency comb. By repeating this procedure over the length of a single-stranded DNA, the sequence of the DNA is determined with high accuracy.

More specifically, the DNA to be analyzed is passed through a transport channel for analysis. The channel is designed to allow DNA to pass through in a substantially uncoiled, or linear, conformation so that each or substantially all the individual nucleotides of the DNA sweep past a location at which interaction occurs between the DNA and one or more discrete monochromatic components of a frequency comb. The results of the analysis provide sequential identification of individual nucleic acids. The DNA can be held in a substantially linear shape by the use of channels in any of a variety of materials, as is described in the literature referred to in more detail below. The skilled artisan appreciates that methods of the invention are useful to analyze any polymer and to obtain the sequence of the monomer units. Examples of other polymers include proteins, nucleic acids, sugars, synthetic polymers and others.

The invention also contemplates the detection of molecular structure in single molecules, in groupings of biological interest, such as codons and genes or specific information bundles by the methods and systems disclosed. The detection process uses recognition patterns obtained from known molecules and sequencing the information generated for a record or data base.

Systems and methods of the invention provide detectors that read, measure, quantify, and detect alterations in various parts or the continuum of a frequency comb used to identify, analyze or quantify molecules, nucleotides, binding sites, abnormalities, sizes and dimensions of targeted biological or molecular structures. In one embodiment, the detector detects missing segments of the light spectrum that are removed either by scattering processes or by absorption.

The detected spectral response may be any light spectrum. Preferred spectra include absorption, reflection, transmission, fluorescent, and chemiluminescent spectra produced through interaction of the frequency comb, or portions thereof, with the target. The spectrum produced by a detection target may be compared to a standard in order to identify the target or its physical or chemical properties.

Due to the speed with which light travels, and the extremely short duration of pulses used, methods of the invention are useful to analyze samples in any state of matter. Thus, gases, liquids, solids, and transitional states are measurable and detectable using methods of the invention. Preferred samples for analysis using methods of the invention include organic and non-organic substances, biological compounds, molecules, atomic structures, and any other compositions upon which light can be projected. In a preferred embodiment, methods of the invention are used to analyze a biological molecule, such as a nucleic acid, including DNA, ribonucleic acid (RNA), peptide nucleic acid (PNA), proteins, or analogs of nucleic acids or proteins. For flow velocities of liquids or gases of conventional value, such as rates in the range of tenths of millimeters per second to meters per second (i.e., a flow rate spanning four orders of magnitude), light pulses operating at rates of 100 MHz (i.e., $10^8$ per second) would sample a flowing substance at a differential position or spacing of from 0.01 Angstrom to 10 Angstroms, or $10^{-3}$ nm to 1 nm.

Methods and materials of the invention are useful to catalyze and to monitor chemical reactions. Light pulsing using frequency combs of the invention is useful to "visualize", through the appropriate spectrum produced by interaction of the elements of a chemical reaction with the frequency comb, the process of a chemical reaction and its components. In one embodiment, multiple frequency combs are used to probe a chemical reaction along the length of a reaction tube or chamber in order to analyze different portions of the reaction.

One of ordinary skill in the art appreciates that there are many alternative configurations that can be used for analyzing physical substrates, both with regard to the substrates and materials to be analyzed, and with regard to the methods and apparatus used to perform the analysis. The invention contemplates any analytical method that relies on the use and detection of optical signals from the ultraviolet through the visible and extending to the infrared. The invention contemplates any feature of optical technology that can provide meaningful information about a substrate or material, including but not limited to absorption, transmission, reflection, refraction and emission of light, observation of features of light such as polarization, phase, index of refraction, transmission velocity, interference, and energy transfer by optical methods.

Methods and materials of the invention are also useful in optical communication technology. In one embodiment, the communication technology is a conventional fiber optic based telecommunication methodology. Each of the large number of frequencies of light present in frequency combs of the invention is useful as a carrier for a separate communication channel, in a system such as a wavelength division multiplexing (WDM) system. A single optical fiber of the conventional type used for telecommunications can support thousands of individual communications simultaneously, each transmitted on a discrete channel. In one embodiment, a communication of information, whether in the form of voice, data, or image, or some combination thereof, is performed using a monochromatic component of a frequency comb as a carrier upon which the information is modulated. The modulated carrier is transmitted by a transmitter and received by a receiver. The information is demodulated from the carrier by the receiver, and the information is provided to a recipient. One of ordinary skill appreciates that the information can be modulated onto the carrier as digital or analog information, and that the information can be transmitted or received by a person using the appropriate output or input device, or by a machine such as a computer or fax machine.

In practice, the invention features methods for transmitting information. Methods of the invention comprise the steps of generating a frequency comb comprising a plurality of monochromatic spectral lines, encoding information using at least one of the spectral lines as a carrier, and transmitting the information to a receiver via an optically transmissive medium.

In yet a further aspect, the invention features a method for receiving optically transmitted information. The method involves receiving information encoded in at least one monochromatic spectral line, wherein the line is a spectral component generated by passing monochromatic illumination through an optical waveguide having one or more constrictions therein.

In some embodiments, the method of transmitting information or the method of receiving information can employ information that is selected from the group consisting of textual information, graphical information, tabular information, visual information, and auditory information.

Further aspects and features of the invention are presented in the following drawings and detailed description.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

The invention provides frequency combs for analysis of materials and for communications. A frequency comb is a plurality of narrow, spaced-apart light emission lines produced from an essentially monochromatic light source. Frequency combs are useful because they provide discrete wavelengths of light separated in space and time for very accurate transmission of information (either information concerning a substrate to be analyzed or optically-encoded information content).

The present invention provides frequency combs that span the entire spectrum, preferably in frequency ranges of the order of an octave having extremely precise wavelengths with very narrow frequency separations between individual pairs of discrete monochromatic components. Frequency combs of the present invention permit the precise measurement of characteristics of materials that are measurable using absorption, emission, reflection, refraction and transmission. In particular, frequency combs of the present invention provide extremely large numbers of discrete lines. In some embodiments the frequency comb comprises millions of discrete monochromatic components or lines. These discrete monochromatic components can be used individually, or they can be combined, to form optical sources that can be tuned to match the characteristics of individual chemical moieties such as atoms, molecules, chemical functional groups, chemical monomers, polymers, ions, salts and/or adducts of molecules. Such optical sources can be designed to excite a response from a known material and to elicit no response or a much diminished response from another known material, thereby providing a convenient method of discrimination between the two materials, or alternatively, a convenient method of analyzing a material for the presence of one or another known chemical moiety.

In practice there are two preferred applications of frequency combs. The first is in the area of substrate analysis. Because frequency combs comprise narrow emission lines that can be pulsed onto a substrate at high frequency, they are useful to detect, identify, and characterize substrates that are not amenable to elucidation with conventional single wavelength light. For example, frequency combs are useful to determine the sequence of nucleic acids, such as DNA, RNA, and PNA. A typical nucleic acid in DNA is of the order of tens of angstroms wide. A typical wavelength of light in the visible parts of the spectrum, such as the wavelength of the maximal intensity of sunlight, has a wavelength of thousands of Angstroms, or hundreds of nanometers. Thus, no matter how rapidly such a wavelength is pulsed onto a nucleic acid, it will never "see" the nucleic acid at a resolution fine enough to distinguish one nucleotide from another (e.g., an adenine from a thymine). Frequency combs have discrete monochromatic components that differ in wavelength, in some embodiments, by only about 0.01 angstroms. The duration of an individual pulse can range from approximately $10^{-12}$ seconds (picoseconds) to $10^{-18}$ seconds (attoseconds). Thus, frequency combs obtain time resolution of individual monomer components of a polymer, such as DNA, by virtue of their size, selection, and pulse rate.

In some embodiments, femtosecond ($10^{-15}$ seconds) pulses coupled with the narrow bands produced in a frequency comb allows detection of nucleic acid sequences through the ability to differentiate the various nucleotides that make up the structure of the nucleic acid. One useful range of pulse durations is the range of about 1 picosecond to less than about 10 femtoseconds. In one embodiment, the differentiation occurs based on the ability or lack thereof of a nucleic acid to interact with a specific wavelength of light. An example is absorption of a discrete wavelength associated with a change in the energy state of the nucleic acid. In another embodiment, the differentiation occurs based on the brevity of duration of a pulse, which at the femtosecond time scale is of the same duration as the time for a molecule to vibrate or to begin to react chemically.

Methods of the invention for sequencing nucleic acids comprise generating a frequency comb as described in detail below and in the figures. A nucleic acid molecule is then linearized using methods known in the art. See, e.g., PCT Published Patent Application WO 96/29593, incorporated by reference herein. The linearized nucleic acid is passed through a channel having a width approximately equal to, but larger than, the width of the linearized DNA. The channel comprises a detection zone in which each nucleotide sequentially passes as the DNA proceeds through the channel. At the detection zone, each nucleotide, or a group of nucleotides, is pulsed with at least one monochromatic component of a frequency comb as described below. An optical response is then measured from each nucleotide, or from a group of nucleotides. The cumulative response based on the pulsed light provides a signature for each nucleotide, or group of nucleotides, in the sequence. Details are provided below.

EXEMPLIFICATION

Example 1

Generation of a Frequency Comb

Figure 1:
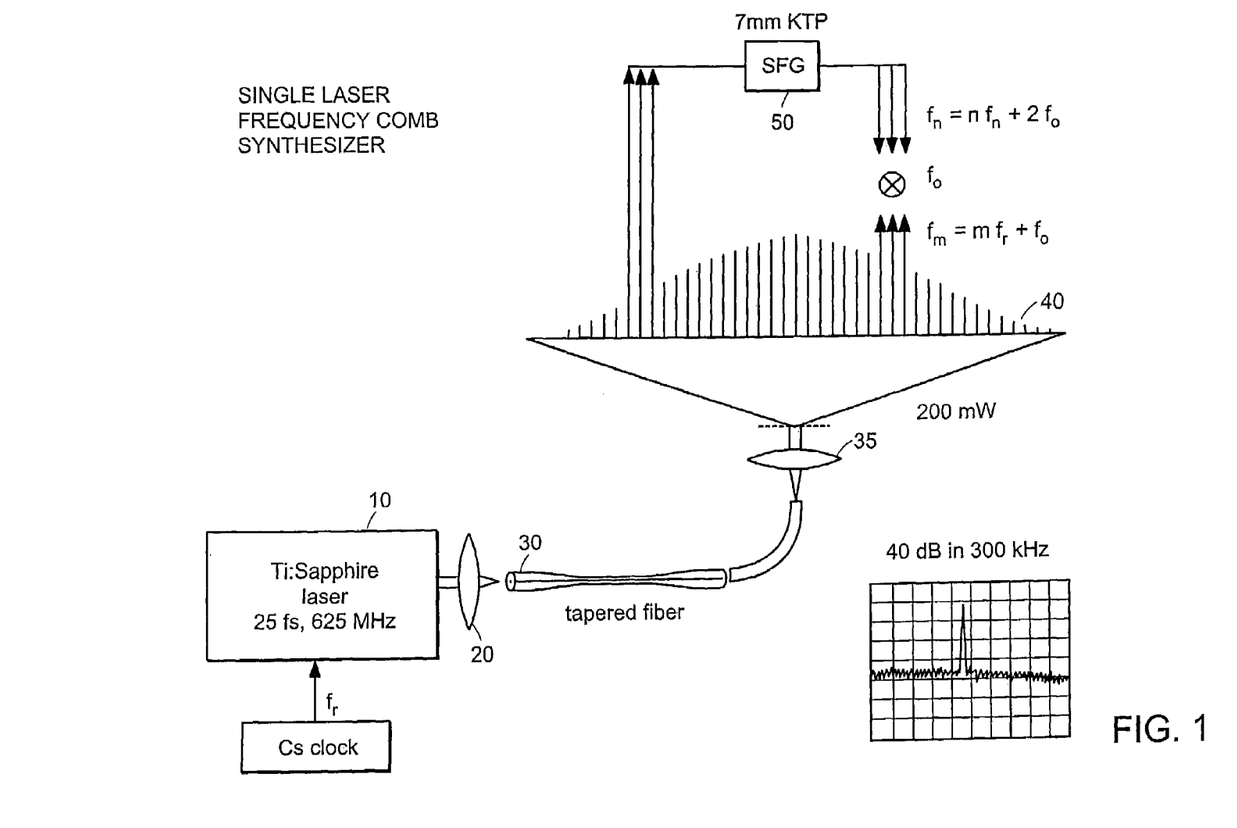
FIG. 1 is a schematic diagram of an exemplary apparatus used to synthesize a frequency comb using a single laser source, according to principles of the invention.

Referring to FIG. 1, a source 10, such as a Titanium (Ti): sapphire ($Al_2O_3$:$Ti^{3+}$) laser, operated in pulsed mode, for example at a frequency of 625 MHz, with a pulse duration of 25 femtoseconds (fs), provides illumination that is focused by a lens 20 into an optical path. The optical path can be an optical fiber 30, such as the tapered optical fiber shown in greater detail in FIG. 2, that has a constriction 32. In one embodiment, the tapered optical fiber 30 has an overall diameter of about 125 micrometers and a constriction 32 (or "waist") having a diameter that is 1.8 micrometers in diameter. In some embodiments, the waist 32 is 1.5 micrometers in diameter. The interaction of the pulsed illumination with the constriction 32 creates a frequency comb 40 ("frequency comb illumination"). The frequency comb illumination exiting the tapered optical fiber 30 is focussed by a lens 35. In one embodiment, the frequency comb illumination contains optical radiation that comprises a series of substantially monochromatic signals having a frequency spacing of about 10 GHz.

The pulse train is controlled at a desired frequency by the clock 38, which controls the pulse rate of the mode-locked laser. The pulses from a mode-locked laser are produced in a periodic train. Therefore, the broad frequency spectrum of the laser is composed of a vast array, or comb, of distinct frequency modes spaced by the cavity repetition rate. In principle, a single pulse would contain an infinite number of distinct frequency modes. The repetition rate R is equivalent to the frequency-domain comb spacing of the emitted pulse train. The repetition rate is determined by the cavity length, L, and the group velocity, $v_g$, of the intracavity pulse according to the relation $R=v_g/(2L)$, or velocity divided by round trip distance. In an exemplary embodiment, a repetition rate is selected by controlling the cavity length, and hence the round trip distance, for example with a transducer such as a piezoelectric transducer that controls a cavity mirror and a control loop that senses a selected harmonic of the repetition rate so as to obtain phase lock.

In one embodiment, a selected substantially monochromatic optical signal impinges on a second harmonic generating crystal 50, such as a 7 millimeter segment of Potassium Titanyl Phosphate (KTP). The frequency doubled radiation emitted therefrom is combined with a second selected frequency, which provides sum and difference radiation frequencies ("beats"), the spacing of which is indicative of the frequency spacing in the frequency comb.

Figure 4:
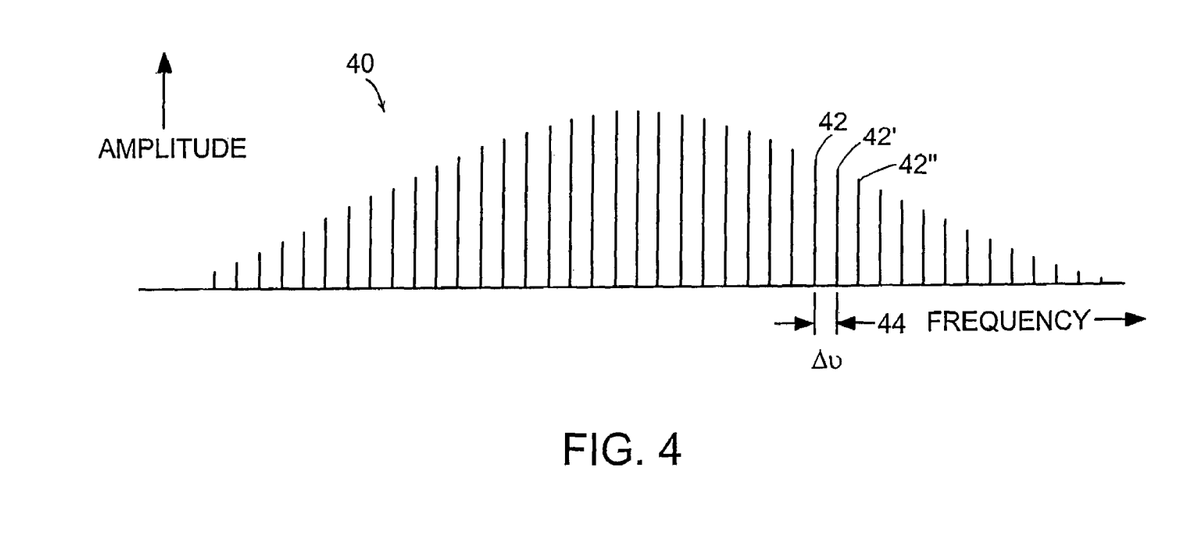
FIG. 4 is a diagram showing the frequency comb 40 shown in FIG. 1 in greater detail.

FIG. 4 is a diagram showing the frequency comb 40 shown in FIG. 1 in greater detail. The frequency comb 40 comprises a plurality of discrete wavelengths $v_1$ 42, $v_2$ 42', $v_3$ 42". The discrete wavelengths $v_1$ 42, $v_2$ 42', $v_3$ 42" are separated one from the other by a spacing $\Delta v$ 44 given as a typical example by $\Delta v = v_2 - v_1$. The range of frequencies in the frequency comb 40 can span an octave (i.e., the highest frequency is at least twice the lowest frequency), or equivalently, in wavelength, the shortest wavelength is no longer than one half the longest wavelength. Frequency combs 40 having more than an octave of bandwidth are possible.

Example 2

Use of a Frequency Comb in Biologically Important Applications

Figure 3A:
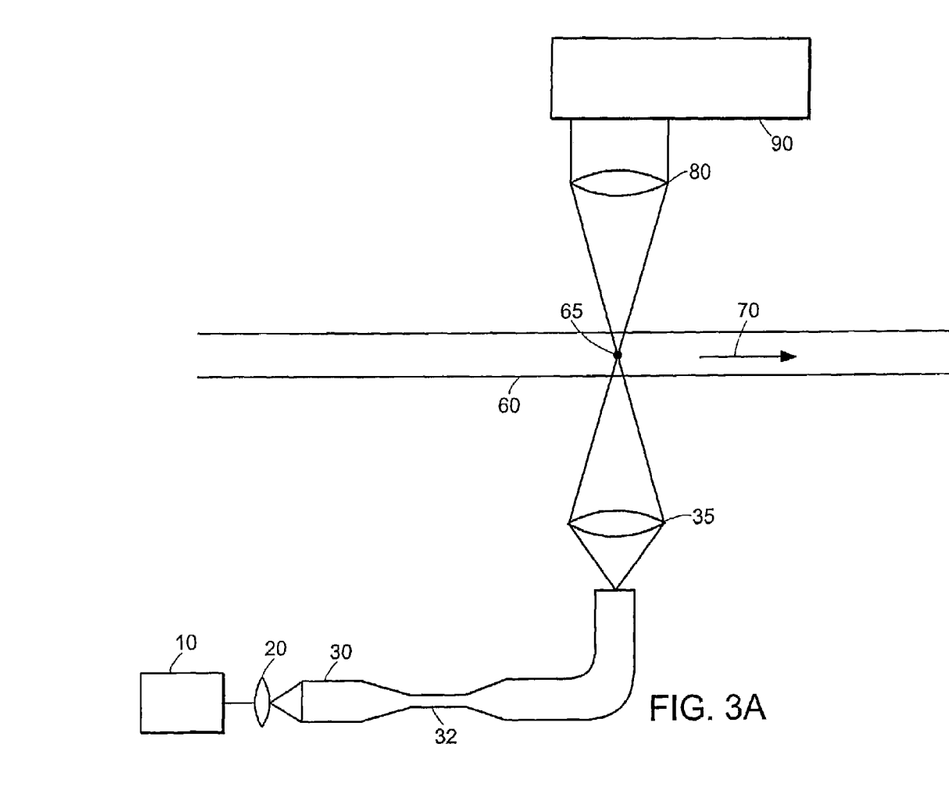
FIG. 3A is a schematic diagram showing an exemplary analytical apparatus, according to principles of the invention.

As shown schematically in FIG. 3A, the frequency comb illumination may be focused onto substantially a point of light 65 that coincides with a point within a channel 60 through which a fluid 70 can flow, as indicated by the arrow 70. The channel is fabricated from a suitably transparent material. The channel 60 carries a fluid 70 comprising a chemical substance to be identified or that is intended to otherwise react with at least a portion of the frequency comb illumination. For example, a solution containing DNA may move down the channel 60 into the illuminated area. As will be discussed in more detail below, the DNA can be caused to move under the action of electric fields, or alternatively the DNA can be carried by a moving carrier fluid. As the frequency comb illumination passes through the channel 60, one or more frequency components of the frequency comb interact preferentially with the chemical substance, such as the individual nucleic acid bases of the DNA. In some embodiments, the interaction is a specific absorption of certain peaks in the frequency comb which are characteristic of the substance. In other embodiments, the interaction can be the excitation of a response from the chemical substance such as when a moiety is labeled with a chromophore. In addition the response may be chemical, such as a chemical reaction, or physical, such as an optical reemission at a specific wavelength. The frequency comb illumination passing through the channel 60 can be detected or observed, with or without beam shaping or focusing with a lens 80. The transmitted frequency comb illumination can for example be observed using a spectrometer or spectrophotometer 90.

In some embodiments, a passageway having an effective diameter of less than approximately 5 nanometers (nm) is provided to maintain single strand DNA material or other polymers of interest (e.g., DNA) for analysis in a linearized form. The literature indicates that linear single-stranded DNA has a diameter of about 1.6 nm, and linear double-stranded DNA has a diameter of about 3.4 nm. The literature indicates that dual-strand DNA in its natural, or folded, configuration is larger that 5 nm in dimension and so will not pass through a passageway of less than 5 nm effective diameter. Equivalently, a passageway of less than 5 nm effective diameter is too narrow to permit the folding of a linearized single or double strand of DNA, The literature describes a number of materials that define suitable passageways or apertures therein. Passages can be generated in flat plate by damaging the plate material, for example by bombardment with charged particles, followed by etching. See for example, R. L. Fleischer, P. B. Price, R. M. Walker, Nuclear Tracks in Solids (Univ. of California Press, Berkeley, Calif. (1975); European patent Application No. 83305268.1; and U.S. Pat. Nos. 3,303,085; 3,662,178; 3,713,921; 3,802,972; 3,852,134, 4,956,219, 5,462,467, 5,564,959 and 5,449,917, each of which is incorporated herein by reference in its entirety.

Various materials comprise passageways or apertures of suitable size when they are manufactured. Examples include arrays of carbon nanotubes (see Iijima, Nature, 354:56 (1991); U.S. Pat. No. 5,457,343; U.S. Pat. No. 5,346,683), and anodic porous alumina (see A. Despic and V. P. Parkhutik, in Modern Aspects of Electrochemistry, J. O. Bockris, R. E. White, B. E. Conway, Eds. (Plenum, New York, 1989), vol. 20, chap. 6; D. AlMawiawi, N. Coombs, M. Moskovits, J Appl. Phys. 70, 4421 (1991); Martin, C. R., Science, 266:1961 (1994)). In addition, anodic porous alumina has been used as a template for making metal structures having the same shape and dimensions (see Matsuda and Fukuda, Science, 268:1466 (1995)). Other porous materials with small pores for use as templates have been described in Ozin, G., Adv. Mater. 4:612 (1992) and in Nishizawa et. al., Science 268:700 (1995). Each of the above-mentioned publications is incorporated herein by reference in its entirety.

Linearized DNA molecules are generated in fluids under the influence of electric fields (see Bustamante, C. 1991. Direct observation and manipulation of single DNA molecules using fluorescence microscopy. Annu. Rev. Biophys. Biophys. Chem. 20:415–46; Gurrieri, S. Rizzarelli, E. Beach, D. and Bustamante, C. 1990. Imaging of kinked configurations of DNA molecules undergoing orthogonal field alternating gel electrophoresis by fluorescence microscopy. Biochemistry 29:3396–3401; and Matsumoto, S., Morikawa, K., and Yangida, M. 1981. Light microscopic structure of DNA in solution studied by the 4',6-diamidino-2-phenylindole staining method. J. Mol. Biol. 152:501–516. Each of the above-mentioned publications is incorporated herein by reference in its entirety.

Reports of linearized DNA passing through passageways under the influence of applied electric fields also appear in the literature (see Kasianowicz, J. J., Brandin, E., Branton, D.; and Deamer, D. W. 1996. Characterization of individual polynucleotide molecules using a membrane channel. Proc. Natl. Acad. Sci. USA. 93:13770–3; and Bezrukov, S. M., Vodyanoy, I., and Parsegian, V. A. 1994. Counting polymers moving through a single ion channel. Nature. 370:279. Each of the above-mentioned publications is incorporated herein by reference in its entirety.

Figure 3B:
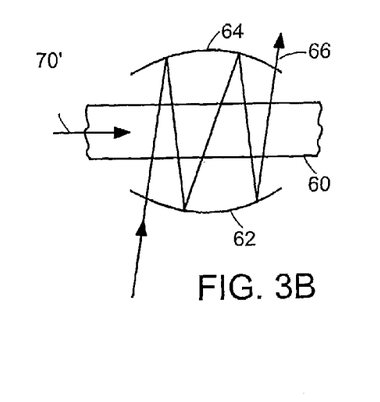
FIG. 3B is a diagram showing an exemplary optical cavity that causes illumination to pass a specimen a plurality of times, according to principles of the invention.

As shown schematically in FIG. 3B, the region surrounding the channel 60' can be an optical cavity 62, 64, within which the frequency comb illumination makes multiple passes through the channel 60', so as to increase an interaction cross-section between the frequency comb illumination and a substance in the channel 60'. For ease of understanding, a single ray 66 of the frequency comb illumination is shown in FIG. 3B.

Figure 2:
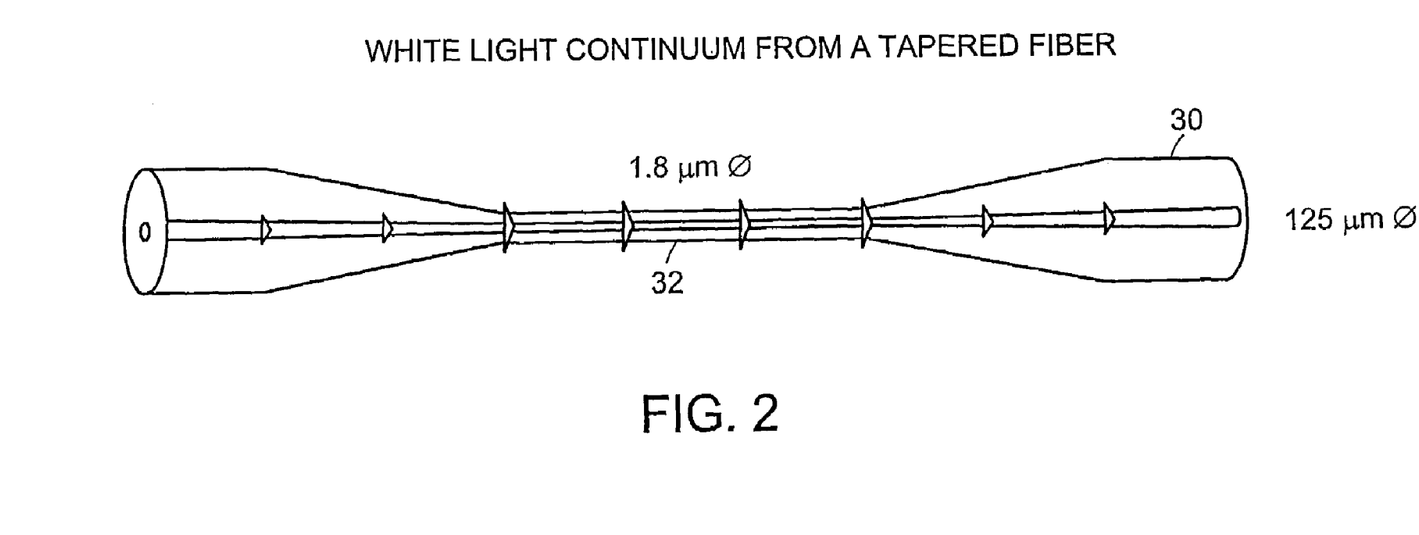
FIG. 2 is a close-up view of an exemplary tapered optical fiber having a constriction therein, according to principles of the invention.

In some embodiments, the end of the optical fiber 30 comprises nanoparticles, such as gold nanoparticles, that interact with the illumination by absorption and re-emission. The presence of nanoparticles modifies the radiation field behavior of the optical fiber 30.

The analysis of the radiation that is transmitted through the channel provides information as to the identity or chemical composition and the concentration of substances in the channel. The signature that results from absorption of selected frequency components of the frequency comb illumination can provide information as to the identity and quantity of a particular substance in the channel. In alternative embodiments, a dual beam geometry can be used to provide a measurement referenced to a defined condition, such as a known quantity of a known substance within fluid in a channel.

Methods and systems of the invention are applicable to a broad range of materials and to a broad range of measurements. Titanium sapphire lasers are tunable with an emission band having a range of approximately 660 nm to approximately 1100 nm. The frequency of the titanium sapphire laser can be increased by factors of integers, such as frequency doubling and frequency tripling the laser light emission, thereby decreasing the emitted wavelength by factors of 2 and 3, respectively. Accordingly, the titanium sapphire laser is useful to generate frequency combs over a range of frequencies. One can also employ other laser sources to generate frequency combs. For example, some Nd:glass and Ytterbium lasers generate pulses in the 10–1000 femtosecond range.

In the field of chemistry, reactions are controlled by providing sufficient energy to overcome reaction barriers. Chemical reactions depend on complex combinations of such features as thermodynamic stability of reagents and products under specific conditions of pressure, temperature and composition (i.e., solvation, pH, the presence of catalysts, and the like), and detailed molecular features such as energy states including ground states and excited states and the associated electronic wavefunction distributions, internuclear or interatomic distances, molecular conformations, and vibrational modes. The preceding list is not intended to be exhaustive, but rather to indicate the range of features that can have an effect on a given chemical reaction. The path of a chemical reaction and the end products that are obtained can be controlled by controlling some or all of the enumerated features, as well as others. In particular, the use of light having particular frequencies and polarization properties can affect the energy states of atoms and molecules. Light of a properly selected frequency and polarization can be absorbed by a chemical substance, which thereby gains energy corresponding to $E=h\nu$. As is well understood in the spectroscopic arts, the change in energy can result in a transition to a different energy state, and/or can result in a change in the interatomic spacing of atoms in a molecule.

Figure 5:
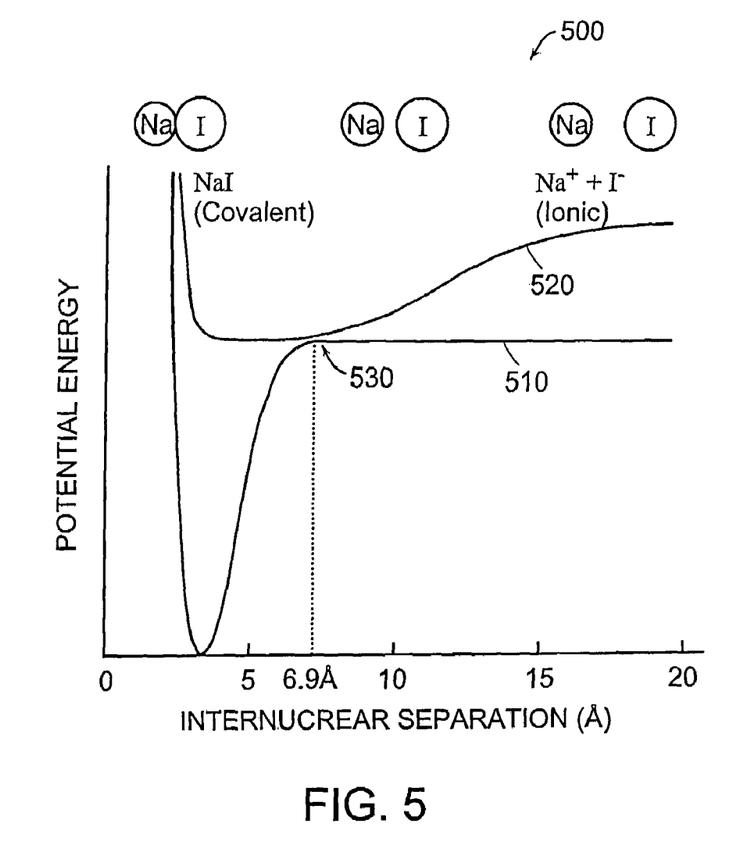
FIG. 5 is an exemplary schematic energy diagram showing the relationship between potential energy and interatomic distance in a molecule.

FIG. 5 is an exemplary schematic energy diagram 500, in which individual curves 510, 520 represent the relationship between potential energy and interatomic distance for a specific electronic state. The diagram is based on theoretical calculations. At a location 530 in the diagram where two curves 510, 520 come close together or actually intersect, the molecule can undergo a spontaneous transition from one energy state to another. Transitions between curves can also be driven by the absorption or emission of a photon having the appropriate energy. The diagram gives as an example data for the material sodium iodide, NaI. In this example, curve 510 is the ground state and curve 520 is the first excited state. The point 530 corresponds to an internuclear distance of 6.9 Angstroms, which represents the internuclear distance at which a state transition is most likely. For more complex materials, it may not be convenient or possible to construct the appropriate theoretical energy diagram. Nevertheless, the conceptual basis for initiating and driving chemical reactions is understandable in terms of applying the correct quantity of energy to a substance in a selected energy state. Prior to the development of an optical source such as the frequency comb 40, which provides discrete monochromatic lines having very closely spaced discrete energies, there has been no practical way to provide precisely tuned, precisely timed energy pulses suitable for use in driving a specific chemical reaction involving a particular molecular entity in a selected energy state.

The invention contemplates the use of the entire light spectra (from IR to UV and the entire range of colors in light combs) to gain molecular and biological information. In one aspect, methods and systems of the invention provide the ability to detect biological and molecular information through the use of "light combs" utilizing the discrete segments in terms of time, distance, light properties and the entire wavelength of a light comb. In one embodiment, methods and systems of the invention use light combs to distinguish biological or molecular information through measured absorption of specific spectra of the light comb. In one embodiment, methods and systems of the invention use light combs to distinguish biological or molecular information through measured, rapidly activated and redundantly activated chemo-luminescence. In one embodiment, methods and systems of the invention use light combs to distinguish biological or molecular information through measured refraction of continuous light wavelength segments. In one embodiment, methods and systems of the invention use light combs to distinguish molecular and biological information through rapidly pulsed discrete fractions of light wavelengths utilizing light combs. In one embodiment, methods and systems of the invention use multiple color markers activated by segments of a light comb as a means of detecting genetic sequences, single nucleotide polymorphisms, single nucleotides, continuum of nucleotides in a specific sequence (such as genes) or groups of 3 nucleotides (such as codons) in DNA or RNA. In one embodiment, methods and systems of the invention use shaped pulses to excite molecules as a means of detection of or identification of the molecule based upon a unique signature of the molecular reaction to its excited state. In one embodiment, methods and systems of the invention identify molecules and information about the molecule using selected combinations of specific color bands from the light comb to elicit a detectable reaction.

Example 3

Use of a Frequency Comb in Optical Communication Applications

In the field of telecommunication, an exemplary frequency comb having a spacing of approximately 50 MHz and a one octave spectral bandwidth from approximately 600 nm to approximately 1200 nm, which is equivalent to a bandwidth extending from $500 \times 10^{12}$ per second or 500 TeraHertz (THz) to 250 THz, (i.e., 250 THz bandwidth), there would be approximately $5 \times 10^6$ or 5 million discrete monochromatic components in the frequency comb. At a frequency separation of 100 MHz, which is a common separation between adjacent channels in present-day telecommunication, the frequency comb would support approximately 2.5 million separate channels. A discussion of some of the features of optical communications appears in U.S. Pat. No. 5,631,758, the entire disclosure of which is incorporated herein by reference. Because the repetition rate can be controlled, as described above, the frequency spacing in the frequency comb can be controlled. For a comb of a given spectral width, such as an octave, one can control the number of monochromatic spectral lines by determining a repetition rate that divides the spectral width into the desired number of segments. For example, repetition rates can be chosen to divide the spectral width into, for example, any of 1,000, 10,000, 100,000, 1,000,000 or 10,000,000 segments The number of monochromatic spectral lines will then be one larger than the number of segments. As those of skill in the art will recognize, the only limitation on the repetition rate is that a mode locked operating condition must be achieved.

One exemplary use of frequency combs of the invention for telecommunication employs an individual monochromatic component of the comb as a carrier upon which information is modulated, and transmitted using an optical transmission medium such as an optical fiber, air, or water, depending on the frequency of the monochromatic component and the optical characteristics of the transmission medium. A receiver receives the optical communication and recovers the information by demodulation. The information is any type of information that can be encoded and transmitted in analog or in digital form. As is understood by those of skill in the optical communication arts, general purpose computer hardware and associated software, or dedicated, custom computer hardware can be employed to modulate, demodulate, and control the transmission of information. The information can be transmitted and/or received using conventional or proprietary data transmission protocols.

The methods and materials of the invention, including apparatus that is used to perform the analysis, or to communicate using frequency combs, are in one embodiment controlled and operated under computer control, using general purpose computers. A general purpose computer, is a commercially available personal computer that comprises a CPU, one or more memories, one or more storage media, one or more output devices, and one or more input devices. The computer is programmed with software comprising commands that when operating direct the computer in the performance of the methods of the invention. Those of skill in the programming arts will recognize that some or all of the commands can be provided in the form of software, in the form of programmable hardware such as flash memory or ROM, in the form of hard-wired circuitry, or in some combination of two or more of software, programmed hardware, or hard-wired circuitry. Commands that control the operation of a computer are often grouped into units that perform a particular action, such as receiving information, processing information or data, and providing information to a user. Such a unit can comprise any number of instructions, from a single command, such as a single machine language instruction, to a plurality of commands, such as a plurality of lines of code written in a higher level programming language such as C++. Such units of commands will be referred to generally as modules, whether the commands comprise software, programmed hardware or hard-wired circuitry, or a combination thereof.

In alternative embodiments, the computer is a laptop computer, a minicomputer, a mainframe computer, an embedded computer, or a handheld computer. The memory is any conventional memory such as, but not limited to, semiconductor memory, optical memory, or magnetic memory. The storage medium is any conventional machine-readable storage medium such as, but not limited to, floppy disk, hard disk, CD-ROM, and/or magnetic tape. The output device is any conventional display such as, but not limited to, a video monitor, a printer, a speaker, and/or an alphanumeric display device. The input device is any conventional input device such as, but not limited to, a keyboard, a mouse, a touch screen, a microphone, and/or a remote control. The computer can be a stand-alone computer or interconnected with at least one other computer by way of a network.

Example 4

Use of a Frequency Comb in Measurement of Optical Frequencies

Figure 6:
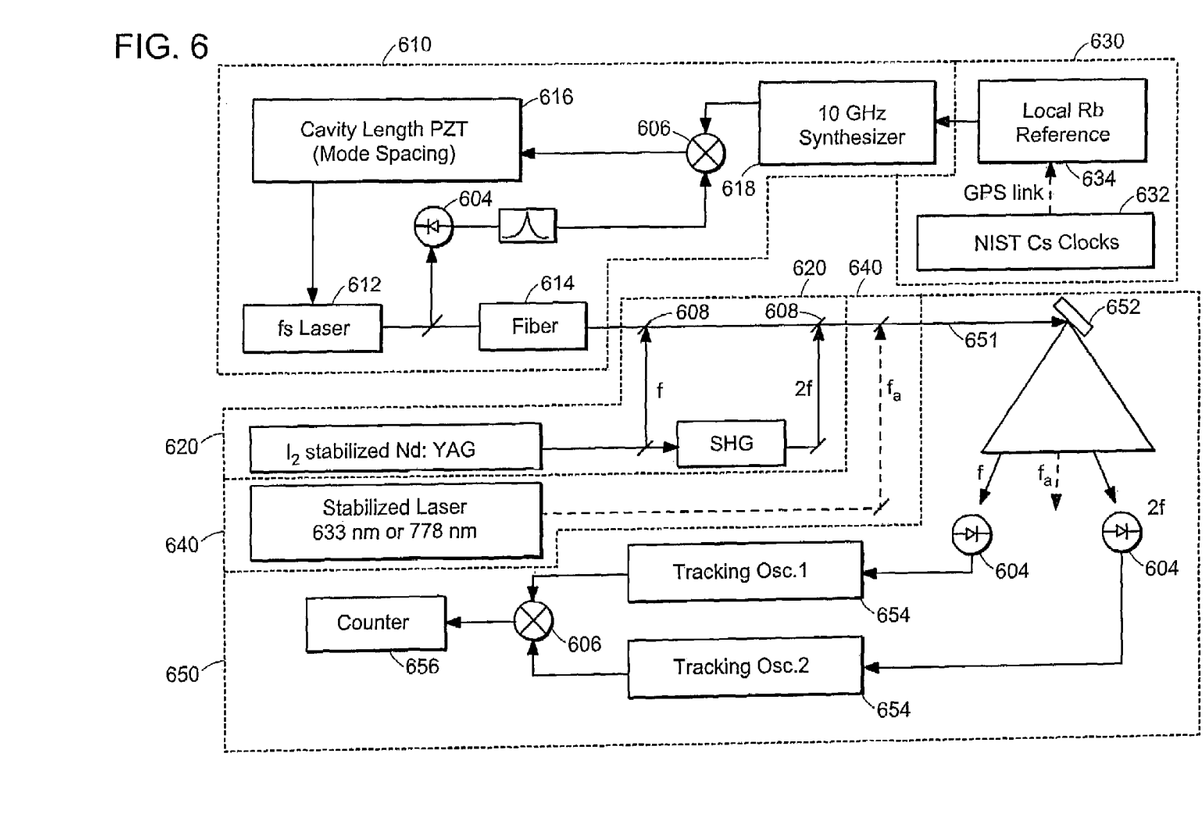
FIG. 6 is a diagram showing an exemplary application of a frequency comb to measuring frequencies of optical sources using a cesium clock microwave standard.

FIG. 6 is a diagram 600 showing an exemplary application of a frequency comb to measuring frequencies of optical sources using a cesium clock microwave standard. In this example, the frequency comb generator is augmented with additional hardware to provide an external reference signal from a cesium clock, as well as laser illumination whose frequency is to be measured. The frequency comb generator is similar to that described in FIGS. 1–4 above. In this example, the generator is the portion of the diagram indicated by the dotted outline 610. A second harmonic generator appears within dotted line 620. The remaining portion of the diagram includes the external standard within dotted line 630, the lasers whose frequencies are to be measured within dotted line 640, and the measuring instrumentation within dotted line 650.

The frequency comb generator comprises a femtosecond laser 612, such as the Titanium-sapphire laser described above, an optical fiber 614 having a constriction of about 1.7 microns diameter and a length in the range of 5 to 10 centimeters (cm), a mode locking device such as a PZT cavity length adjuster 616, and a pulse rate controller such as the 10 GHz synthesizer 618. The second harmonic generator 620 comprises a laser sources 622 such as a Nd:YAG laser and a second harmonic generator crystal 624 such as KTP. As is understood by those of skill in the optical frequency arts, the laser 622 emits light at frequency f and the second harmonic generator absorbs some of the frequency f light and re-emits light at frequency 2f. The external standard comprises a reference clock 632 such as the NIST Cesium clocks at Boulder, Colo., and a local reference 634, such as a Rubidium clock, situated near the frequency comb generator. The lasers 642 whose frequencies are to be measured generate light with frequency $f_a$. The frequency $f_a$ is what is to be measured. The light from the laser 642 is added to the optical beam 651 that comprises the frequency comb and the first and second harmonics f and 2 f, The measuring instrumentation comprises a grating 652 to disperse the components of the optical beam 651, and two detectors 604 whose outputs are beat patterns that are combined and are observed by a counter 656. Not shown is computational equipment that analyzes and displays various signals to confirm the proper operation of the apparatus and the test results. The frequency of the laser under test is determined by computing the offsets of the laser frequency from known frequencies calibrated with the cesium clock microwave frequency.

As is commonly done in the optical arts, components that are commonly used are shown without, appreciable discussion. These components include detectors 604 such as photodiodes, mixers 606 denoted by circles containing an "x," and semi-transparent mirrors 608 that denoted by short solid lines placed at approximately 45 degrees to a beam line, appear at several locations in FIG. 6. Their meaning and use is well known in the art. Arrowheads denote the direction of propagation of electrical and optical signals in FIG. 6

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for generating a frequency comb comprising a plurality of monochromatic spectral lines having defined spacing in frequency space, the method comprising the steps of:

operating a laser in a pulsed, mode locked manner;

controlling a repetition rate, R, of said laser by controlling selected one of a group velocity of light and a cavity length, where said repetition rate is given by the equation R=group velocity/(2 times the cavity length); and passing a train of laser pulses from said laser through an optical transmission medium having a constriction therein, generating thereby a frequency comb comprising a plurality of monochromatic spectral lines having defined spacing in frequency space, the spacing being equal to the repetition rate of said laser.

2. The method of claim 1, wherein said plurality comprises at least 1,000 monochromatic spectral lines.

3. The method of claim 1, wherein said plurality comprises at least 10,000 monochromatic spectral lines.

4. The method of claim 1, wherein said plurality comprises at least 100,000 monochromatic spectral lines.

5. The method of claim 1, wherein said plurality comprises at least 1,000,000 monochromatic spectral lines.

6. The method of claim 1, wherein said plurality comprises at least 10,000,000 monochromatic spectral lines.

* * * * *